United States Patent [19]
McIntyre et al.

[11] Patent Number: 5,994,901
[45] Date of Patent: Nov. 30, 1999

[54] MAGNETIC RESONANCE LOGGING INSTRUMENT

[75] Inventors: Peter M. McIntyre, College Station, Tex.; Weijun Shen, Oak Ridge, Tenn.; Dan A. Gross, College Station, Tex.

[73] Assignee: Global Petroleum Resouces Institute, College Station, Tex.

[21] Appl. No.: 09/078,900

[22] Filed: May 13, 1998

[51] Int. Cl.⁶ .................................................. G01V 3/00
[52] U.S. Cl. .......................................... 324/303; 324/318
[58] Field of Search ................................. 324/303, 300, 324/314, 318, 322

[56] References Cited

U.S. PATENT DOCUMENTS

| | | | |
|---|---|---|---|
| 4,350,955 | 9/1982 | Jackson et al. | 324/303 |
| 4,987,368 | 1/1991 | Vinegar | 324/303 |
| 5,710,511 | 1/1998 | Taicher et al. | 324/303 |

*Primary Examiner*—Louis Arana
*Attorney, Agent, or Firm*—Stacy S. Cook, Esq.

[57] ABSTRACT

A magnetic resonance logging instrument is provided. The magnetic resonance logging instrument (10) may comprise a superconducting magnet system (12) operable to produce a static magnetic field and disposed within a housing (19). An antenna system (14) operable to produce and sense a radio frequency magnetic field may be disposed, in part, within the housing (19) and coupled to the superconducting magnet system (12). A cryogenic cooling system (16) operable to cool the superconducting magnet system (12) may also be disposed within the housing (19). A power system (18) operable to supply power to the superconducting magnet system (12), the antenna system (14), and the cryogenic cooling system(16) may also be provided.

14 Claims, 4 Drawing Sheets

MAGNETIC RESONANCE LOGGING INSTRUMENT

TECHNICAL FIELD OF THE INVENTION

The present invention relates generally to oil field downhole logging tools, and more particularly to a magnetic resonance logging instrument.

BACKGROUND OF THE INVENTION

Magnetic resonance logging instruments are often used in oil field applications to determine the various properties of an earth formation. The magnetic resonance logging instrument is lowered into a bore-hole and non-intrusively measures the various properties in the different strata of the earth formation. The measurements can determine various petrophysical properties of the fluids in the earth formation, as well as providing information about the porosity, permeability, and wetability in the earth formation. Most importantly, magnetic resonance measurements can be used to separately identify and map the oil, water, and other constituents within the earth formation.

Magnetic resonance logging instruments generally operate by first locally placing the earth formation in a static background magnetic field, in which the unpolarized magnetic moments of the hydrogen atoms in the earth formation precess at a characteristic frequency. A polarizing pulse of radio-frequency power is then applied to the earth formation at this same frequency, causing the magnetic moments of the hydrogen atoms to align in a common direction. The polarizing pulse is then turned off, and the time in which this signal decays is the relaxation time "T1." An antenna is used to detect the radio-frequency signal from the precessing polarization of the hydrogen atoms in the earth formation, and the rate in which this signal decays is the free induction decay "T2." T1 and T2 are a sensitive measure of the physical and chemical environment that the hydrogen atoms are located. For example, T1 and T2 can be used to determine whether the hydrogen atoms are part of a water molecule or in a hydrocarbon, and whether the hydrogen atoms are tightly bound in a micro porous region or part of a larger fluid volume. The pulse-and-listen process described above can be repeated to produce a spin echo of the first pulse, which provides enhanced analyzing power.

Conventional magnetic resonance logging instruments utilize a single permanent magnet within the logging instrument to produce the magnetic field. The permanent magnet only provides a magnetic field strong enough to measure the properties of the earth formation approximately twenty centimeters into the earth formation. At twenty centimeters the properties of the earth formation have been compromised by the drilling operation and drilling fluids utilized to produce the well. Accordingly, conventional magnetic resonance logging instruments are not capable of peering into the earth formation past the zone affected by drilling operations. In addition, conventional magnetic resonance logging instruments must proceed at very slow speeds in order to take measurements. The slow speed drastically increases the amount of time to fully log a well.

In addition, conventional magnetic resonance logging instruments cannot readily distinguish oil from water. In order to distinguish between oil and water, the instrument requires a region of relatively uniform magnetic field within the earth formation. Conventional magnetic resonance logging instruments do not provide such a uniform magnetic field.

Furthermore, conventional magnetic resonance logging instruments cannot readily distinguish between hydrogen atoms from sodium atoms. The resonate frequency of sodium atoms is a multiple of the resonate frequency of hydrogen atoms and causes an aliasing signal that is indistinguishable from the hydrogen signal.

SUMMARY OF THE INVENTION

Accordingly, a need has arisen in the art for an improved magnetic resonance logging instrument. The present invention provides a magnetic resonance logging instrument that substantially reduces problems associated with prior systems and methods.

In accordance with one embodiment of the present invention, a magnetic resonance logging instrument is provided. The magnetic resonance logging instrument includes a superconducting magnet system contained within a housing. The superconducting magnet system operates to produce a static magnetic field. An antenna system operates to produce and sense a radio frequency magnetic field. A cryogenic cooling system is contained within the housing and cools the superconducting magnet system. A power system supplies power to the superconducting magnet system, the antenna system, and the cryogenic cooling system.

Technical advantages of the present invention include providing a magnetic resonance logging tool which may produce an increased magnetic field strength as compared to conventional magnetic logging tools. This increased field strength allows the measurement of earth formations outside of the zone affected by drilling operations.

Another technical advantage of the present invention is that the magnetic resonance logging tool may be have a multipole configuration such that hydrogen atoms can be readily differentiated from sodium atoms, thereby eliminating aliasing.

Another technical advantage of the present invention is that the magnetic resonance logging tool may provide a more uniform magnetic field than conventional magnetic logging tools, making it possible to differentiate between oil and water within earth formations being measured.

Another technical advantage of the present invention is that superconducting bump magnets may extend along the longitudinal length of the magnet system, increasing the strength of the magnetic field. Accordingly, magnetic resonance measurements can be taken over a longer length of the magnetic resonance logging instrument. The extended length also allows the magnetic resonance measurements to be taken using a phased array approach, thereby increasing the speed and accuracy of magnetic resonance measurements as compared with conventional magnetic logging tools.

Another technical advantage of the present invention is that a cryogenic cooling system may be provided to maintain the temperature of the superconducting magnet system below the critical temperature.

A further technical advantage of the present invention is that an internal fuel cell may be used to supplement the power requirements of the magnetic resonance logging tool.

Still another technical advantage of the present invention is that the housing of the magnetic resonance logging tool may be fabricated from a laminate of conducting and high-strength, non-conducting washers such that the housing is non-conducting across its longitudinal length.

Other technical advantages will be readily apparent to one skilled in the art from the following figures, descriptions, and claims.

BRIEF DESCRIPTION OF THE INVENTION

For a more complete understanding of the present invention and its advantages thereof, reference is now made to the following description taken in conjunction with the accompanying drawings, wherein like reference numerals represent like features, in which.

DETAILED DESCRIPTION OF THE INVENTION

FIGS. 1 through 8 illustrate a magnetic resonance logging instrument in accordance with one embodiment of the present invention. As described in more detail below, the magnetic resonance logging instrument utilizes a superconducting magnet system to substantially increase the strength of the magnetic field. The increased field strength allows magnetic resonance measurements to be taken outside of the zone affected by drilling operations. The superconducting magnet system may also comprise superconducting bump magnets that extend the longitudinal length and increase the strength of the magnetic field. Accordingly, magnetic resonance measurements can be taken over a longer length of the magnetic resonance logging instrument. The extended length also allows for a phased array approach to taking the magnetic resonance measurements, thereby improving the accuracy of the magnetic resonance measurements and the speed by which they are made. Furthermore, the magnetic field produced by the superconducting magnet system can be altered to a multipole configuration such that hydrogen atoms can be readily differentiated from sodium atoms, thereby eliminating aliasing. Moreover, a cryogenic cooling system is used to maintain the temperature of the superconducting magnet system below the critical temperature. Furthermore, an internal fuel cell may be used to supplement the power requirements of the magnetic resonance logging tool. Additionally, the housing may be fabricated from a laminate of conducting and non-conducting washers such that the housing is non-conducting across its longitudinal length.

Figure 1:
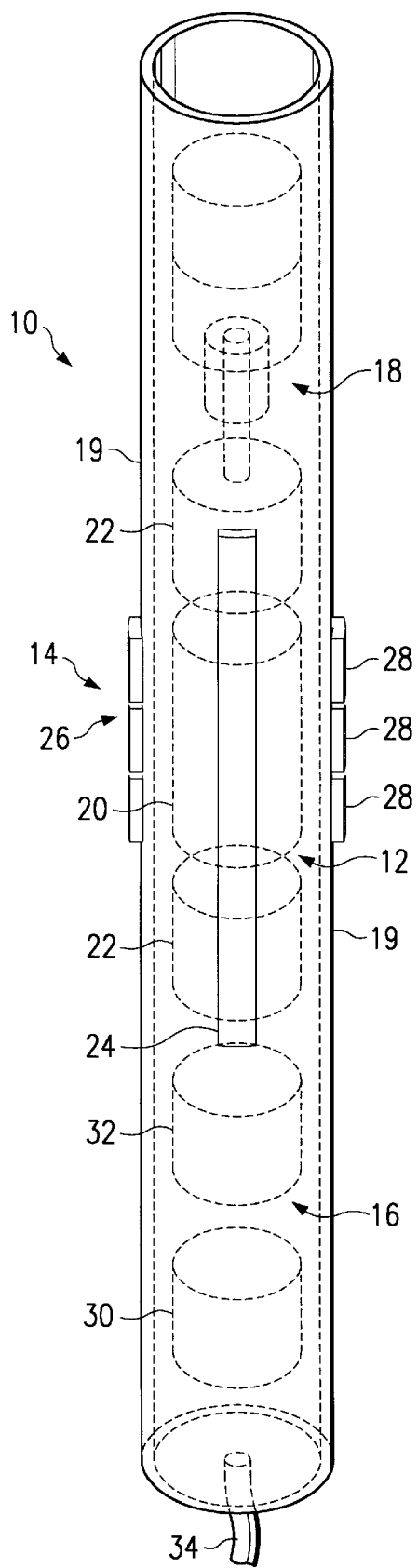
FIG. 1 is an isometric view of a magnetic resonance downhole logging instrument in accordance with the present invention.

FIG. 1 is an isometric drawing of a magnetic resonance logging instrument 10 in accordance with one embodiment of the present invention. Although the magnetic resonance logging instrument 10 is described in terms of an oil field downhole logging instrument, the present invention may be used in any other suitable application without departing from the scope of the present invention. For example, the present invention may be utilized in any application that requires the use of magnetic field external to the body of the instrument to take magnetic resonance measurements.

Referring to FIG. 1, the magnetic resonance logging instrument 10 comprises a superconducting magnet system 12, an antenna system 14, a cryogenic cooling system 16, a power system 18, and a housing 19. The superconducting magnet system 12, as will be described in greater detail below, generates a static magnetic field. In one embodiment, the superconducting magnet system 12 comprises a main superconducting magnet 20. In another embodiment, the superconducting magnet system 12 comprises the main superconducting magnet 20 and a pair of bump superconducting magnets 22, one disposed at each end of the main superconducting magnet 20. The bump superconducting magnets 22 increase axial symmetry of the magnetic field and help produce a 99% uniform magnetic field over 65% of the longitudinal length of the main superconducting magnet 20.

The superconducting magnet system 12 produces a higher strength magnetic field than can be achieved with conventional permanent magnets. In one embodiment, the pure dipole magnetic field strength is calculated to be approximately 200 Gauss at 60 cm, over ten times greater than the magnetic field strength produced by conventional permanent magnets.

The antenna system 14, as will be described in greater detail below, operates to transmit and sense a radio-frequency (RF) magnetic field signal. In one embodiment, the antenna system 14 comprises a drive antenna 24 that produces a drive RF magnetic field, and a sense antenna 26 that senses an RF magnetic field. In a particular embodiment, the sense antenna 26 comprises a segmented sense antenna 28 that operates as a phased array antenna.

The cryogenic cooling system 16, as will be described in greater detail below, operates to cool the superconducting magnet system 12 below the superconductive material critical temperature. In one embodiment, the cryogenic cooling system 16 comprises fuel and oxidizer cryogenic tanks 30 and 32 containing cryogenic liquids. The fuel and oxidizer cryogenic liquids are used to maintain a thermal barrier around the superconducting magnet system 12. Depending on the critical temperature of the superconductive material utilized in the superconducting magnet system 12, a refrigeration system 17 may then be used to further reduce the temperature of the superconducting magnet system 12 to a range of 4 K–20 K.

The power system 18 supplies electricity to the magnetic resonance logging instrument 10. The power system 18 may be external or a combination of external and internal. External power refers to electricity received from an external source, such as a logging truck (not expressly shown) at the surface of the borehole. The external power is transmitted to the magnetic resonance logging instrument 10 by power cables that form a part of the tether 34. Internal power refers to electricity generated within the magnetic resonance logging instrument 10. As will be described in greater detail below, internal power may be generated by using the hydrogen and oxygen from the cryogenic cooling system 16 as fuel for a fuel cell. The fuel cell produces DC electricity and water. The water is either stored or discharged.

The housing 19, as will be described in greater detail below, is a cylindrical shell that supports a hard vacuum on the interior of the housing 19 against the extreme high temperatures and pressures found outside of the housing 19 in the downhole environment. The housing 19 may be non-conductive across its longitudinal length in order to improve the performance of the antenna system 14.

It will be understood that the magnetic resonance logging instrument 10 may comprise other suitable components and systems without departing from the scope of the present invention. For example, the magnetic resonance logging instrument 10 may include an internal computer system that operates to control the internal operation of the magnetic resonance logging instrument 10 and to perform initial signal processing operations on the received magnetic resonance data.

Figure 2A:
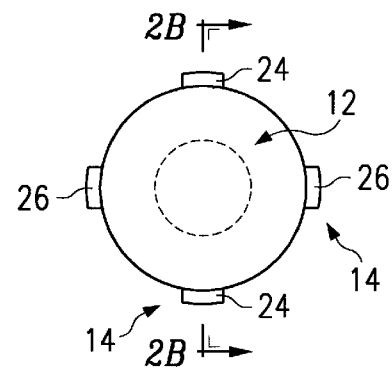
FIG. 2A is an end view of the magnetic resonance logging instrument shown in FIG. 1, and illustrates an antenna system in accordance with the present invention.
Figure 2B:
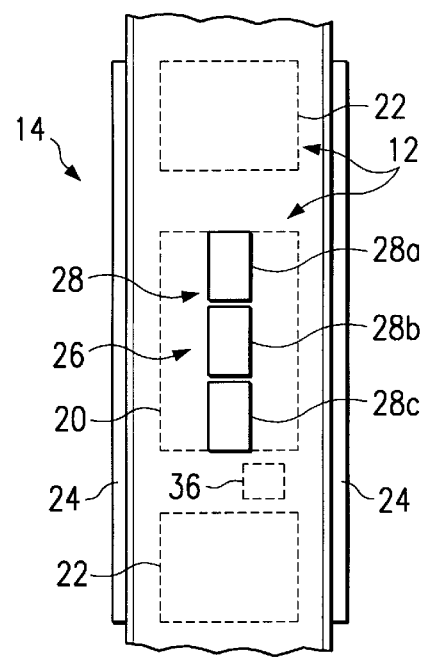
FIG. 2B is a side view of the antenna system shown in FIG. 2A as viewed by line 2B—2B.

FIG. 2A is an end view of the magnetic resonance logging instrument 10, and illustrates the antenna system 14. FIG. 2B is a side view of the antenna system 14 as viewed from line 2B shown of FIG. 2A. Referring to FIGS. 2A and 2B, the antenna system 14 operates to transmit and sense an RF magnetic field signal. As illustrated, the separate drive antenna 24 and sense antenna 26 are configured in quadruture such that the drive RF magnetic field, the sense RF magnetic field, and the static magnetic field produced by the superconducting magnet system 12 are mutually orthogonal. In this configuration, there is no mutual inductance between the drive antenna 24, the sense antenna 26, and the static magnetic field. Accordingly, the sense antenna 26 will only sense the RF signal from resonant magnetic moments in the earth formation. Conventional magnetic resonance logging instruments often utilize a single antenna that serves the dual purpose of a drive and sense antenna. The single antenna for the drive and sense functions often results in a cross-coupling effect that produces a signal from the drive function of the single antenna that is directly sensed by the antenna. The drive signal component must then be removed by signal processing procedures.

The drive antenna 24 is a single antenna that extends the entire length of the superconducting magnet system 12. The drive antenna 24 is coupled to the superconducting magnet system 12. The sense antenna 26 is coupled to a signal conditioning package 36 which may include an amplifier, a data signal processor, and a communication system. The magnetic resonance measurement data is transmitted to the surface of the borehole over communication lines that are incorporated into the tether 34.

The segmented sense antenna 28 allows separate magnetic resonance measurements to be taken on the same target as the target moves past each segment of the segmented sense antenna 28. The segmented sense antenna 28 increases the time that the target material is subject to magnetic resonance measurements. The segmented sense antenna 28 also increases the rate at which the magnetic resonance logging tool 10 can descend in the borehole. In addition, the segmented sense antenna allows the target material to be the subject of multiple magnetic resonance measurements during multiple drive pulses. Accordingly, the magnetic resonance measurements are more accurate.

In one embodiment, the segmented sense antenna 28 is segmented into three individual sense antenna's 28a, 28b, and 28c. The individual sense antennae 28a, 28b, and 28c are coupled to the signal conditioning package 36. Signal processing of the magnetic resonance measurements from the segmented sense antenna 28 may provide magnetic resonance imaging information.

It will be understood that the antenna system 14 may comprise other configurations and systems without departing from the scope of the present invention. For example, the segmented sense antenna 28 may comprise more than three individual segments.

Figure 3:
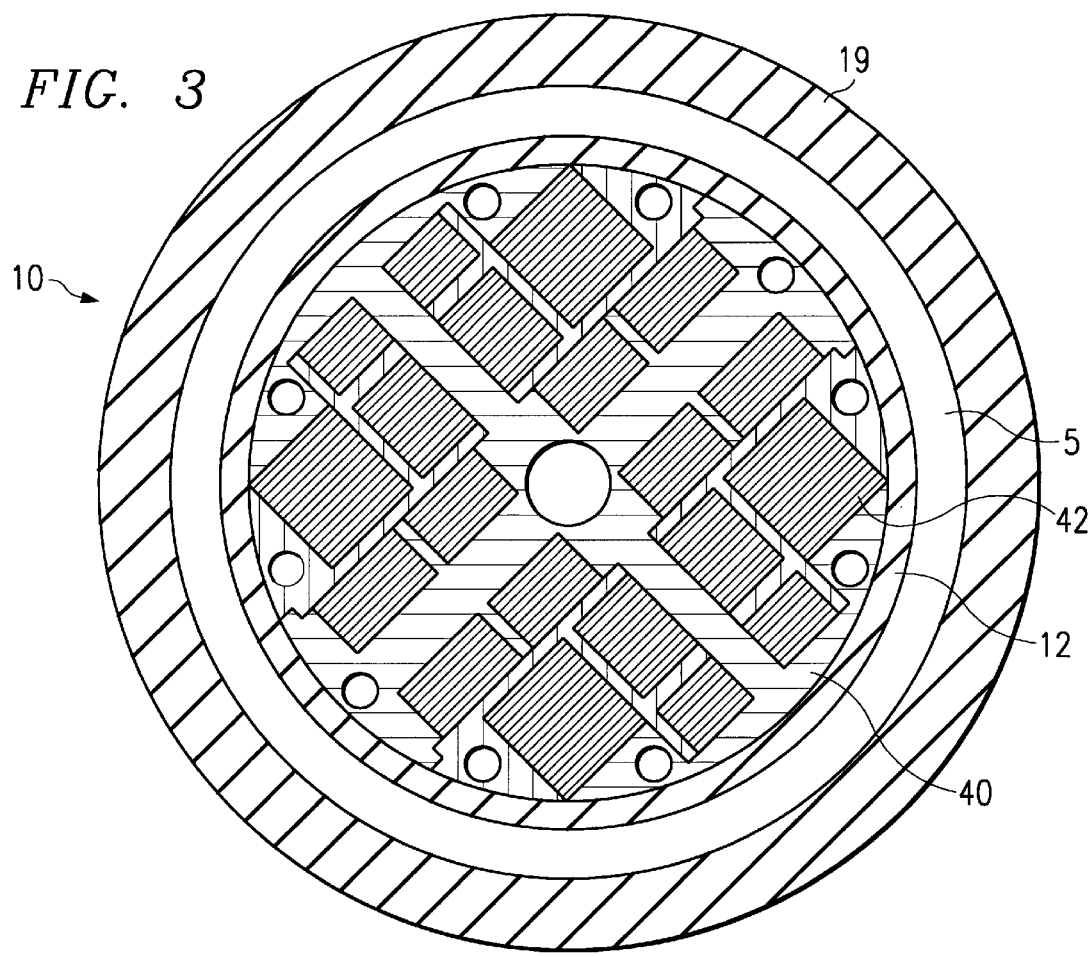
FIG. 3 is a cross-sectional drawing of the magnetic resonance logging instrument shown in FIG. 1, and illustrates a superconducting magnet system in accordance with the present invention.

FIG. 3 is a cross-sectional drawing of the magnetic resonance logging instrument 10, and illustrates the superconducting magnet system 12. As discussed previously, the superconducting magnet system 12 produces a very strong static magnetic field. The superconducting magnets 20 and 22 comprise a superconducting coil 40. The superconducting coil comprises a number of individual windings 42. The windings 42 are generally formed from a bundle of superconducting wires (not expressly shown) having a superconductive material within the superconducting wire.

The superconducting magnets 20 and 22 are individually fabricated. Each winding 42 in the superconducting magnets 20 and 22 may be wound in a racetrack format. The windings 42 are layer wound with turns tightly packed for maximum current density. The individual superconducting wires (not expressly shown) used to fabricate each winding 42 may be FORMVAR™ insulated for turn-to-turn electrical isolation. The windings are integrated into a rigid structural form and impregnated to form the superconducting coil 40.

Various types of superconductive materials are commercially available. High temperature superconductive (HTS) materials are available, and provide the advantage of a critical temperature that is higher than many other superconductive materials. However, high temperature superconductive materials are fragile and cannot conduct as high of an electrical current as low temperature superconductive materials.

The magnetic field produced by the superconducting magnetic system 12 depends upon the individual magnetic fields produced by each winding within the superconducting magnets 20 and 22. The configuration of the superconducting magnet system 12 may be varied by varying the direction that the electrical current is conducted through individual windings 42.

In one embodiment, the superconducting magnet system 12 is configured as a pure dipole magnet such that the electrical current is moving the same direction through each of the windings 42 in the superconducting magnets 20 and 22. The pure dipole configuration has the advantage of optimizing the magnitude and the orientation of the static and RF drive field. This results in a large sensitive volume, optimum signal/noise ratio, and a minimum sensitivity to the alignment of the magnetic resonance logging instrument 10 within the borehole. However, the pure dipole configuration has the disadvantage that signals from sodium atoms at half the target material radius will be fully resonant at the same frequency. In other words, any sodium atoms at one-half the radius of the active magnetic field will resonate and be indistinguishable from hydrogen atoms. As described previously, this condition is known as aliasing.

In another embodiment, the superconducting magnet system 12 is configured as a quadrupole such that the electrical current in adjacent cross-sectional quadrants are in different directions. The quadrupole configuration provides a static magnetic field that is different from that of a pure dipole configuration. The quadrupole configuration offers the advantage of reducing or eliminating aliasing. However, a quadrupole configuration reduces the long-range static magnetic field, so that the effective radius of the magnetic field is reduced.

In a particular embodiment, as illustrated in FIG. 3, the superconducting magnet system 12 is configured as a multipole. The multipole configuration is formed by intermixing the quadrupole and dipole configurations by varying the direction of electrical current flowing through the various windings 42. As will be discussed in greater detail below, the multipole configuration allows the magnetic field to be optimized to achieve maximum penetration into the earth formation and to reduce or eliminate aliasing.

The superconducting magnet system 12 may be fabricated to allow the superconducting magnet system 12 to be switched between various configurations, thereby providing maximum flexibility of the magnetic resonance logging instrument 10. Specifically, in the embodiment illustrated in FIG. 3, ten windings 42 are fabricated, of these, five of the windings 42 are dedicated to a single polarity and the remaining five windings 42 are used to create three separate configurations. These three configurations include a maximum dipole field configuration, a maximum homogeneous volume configuration, and a maximum radius without the possibility of sodium aliasing configuration. Each of these configurations are derived by coil helicity flip which in effect produces interfering dipole and quadrupole magnetic fields.

One embodiment of the superconducting magnet system 12 includes the bump superconducting magnets 22 at each end of the main superconducting magnet 20. As discussed previously, the bump superconducting magnets 22 extend the active static magnetic field and allow multiple magnetic resonance measurements to be taken of the same target material, or the target material can travel at a faster rate past the antenna system 14. The bump superconducting magnets 22 may be fabricated as discussed above.

The electrical current in the bump superconducting magnets 22 is adjusted to produce a magnetic field that corrects the sag in the magnetic field from the main superconducting magnet 20. In addition to correcting the sag in the magnetic field of the main superconducting magnet 20, the active uniform-field zone of the magnetic resonance logging instrument 10 is extended. In a particular embodiment, the bump superconducting magnets 22 are wound with a niobium-tin ($Nb_3Sn$) in order to take advantage of the high current density and higher critical temperature of niobium-tin superconductive materials. This embodiment allows an extension of the 1 percent homogeneous volume from approximately 24 centimeters, with no bump superconducting magnets 22, to approximately 91 centimeters with the bump superconducting magnets 22. Thereby yielding a gain in the sensitive volume by a factor of nearly four. The magnetic field is also increased in strength by the bump superconducting magnets 22, in this same embodiment, the magnetic field increases from 181 Gauss, with no bump superconducting magnets 22, to 210 Gauss with the bump superconducting magnets 22.

It will be understood that the superconducting magnet system 22 may include other devices or systems without departing from the scope of the present invention.

Figure 4:
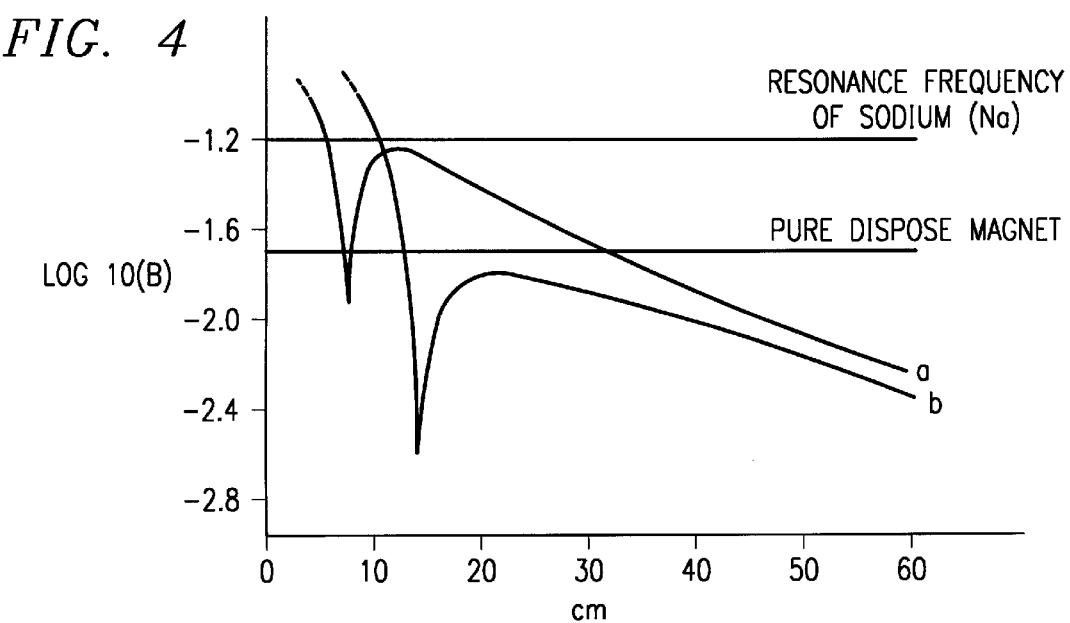
FIG. 4 is a graph illustrating the magnetic field strength at various distances from the superconducting magnet system in accordance with the present invention.

FIG. 4 is a graph illustrating the magnetic field strength at various distances from the superconducting magnet system 12, with different multipole configurations. Graph line "a" corresponds to a superconducting magnet system 12 configuration that obtains a maximum radius magnetic field without the possibility of sodium aliasing. Although the radius of the magnetic field is reduced, this configuration still allows magnetic resonance measurements, i.e. T1 and T2, to be taken outside of the zone affected by drilling operations.

Graph line "b" corresponds to a configuration that allows magnetic resonance imaging of the target material. Magnetic resonance imaging is different than magnetic resonance measurements. Magnetic resonance imaging provides enhanced information about the target material and in conjunction with the segmented sense antenna 28, may provide a synthetic aperture.

Figure 5:
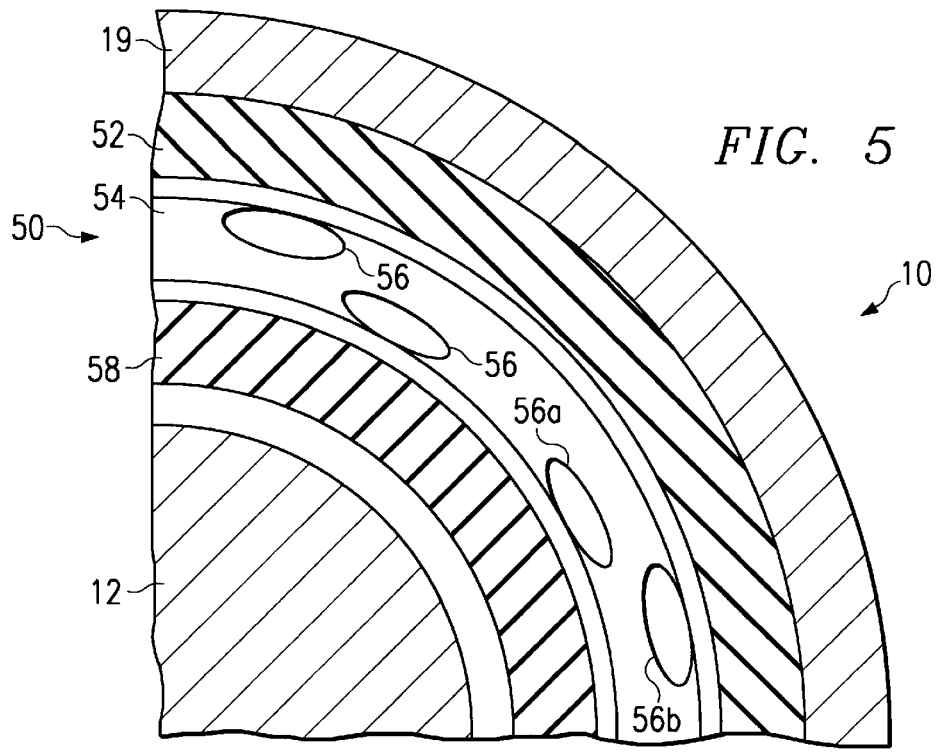
FIG. 5 is a cross-sectional diagram of the magnetic resonance logging tool shown in FIG. 1, and illustrates a portion of a cryogenic cooling system in accordance with the present invention.

FIG. 5 is a cross-sectional diagram of the magnetic resonance logging tool 10, and illustrates a portion of the cryogenic cooling system 16. The cryogenic cooling system 16 comprises a shielding system 50 that is used in conjunction with the cryogenic liquids stored in the oxidizer and fuel cryogenic tanks 30 and 32, respectively. As discussed previously, the cryogenic tanks 30 and 32 contain cryogenic fluids that have cryogenic boiling points. In one embodiment, the cryogenic fluids are liquid hydrogen and liquid oxygen. Liquid hydrogen has a boiling point of approximately 20 K, and liquid oxygen has a boiling point of approximately 90 K.

The shielding system 50 includes a series of thermal barriers to shield the superconducting magnet system 12 from the high temperature environment of the borehole and maintain the superconducting magnet system 12 at a temperature below the required critical temperature. In one embodiment, the shielding system 50 comprises an outer insulation layer 52 disposed between the housing 19 and the superconducting magnet system 12. The outer insulation layer 52 may comprises a vacuum layer (not expressly shown) in combination with a number of superinsulation layers (not expressly shown). The outer insulation layer 52 intercept the radiative heat load from the housing 19.

A middle shield 54 may be disposed inwardly from the outer insulation layer 52. The middle shield 54 may comprise a cooling jacket 56 that receives cryogenic fluids and allows the cryogenic fluids to boil, thereby dissipating the heat load received from the outer insulation layer 52. In a particular embodiment, the middle shield 54 comprises multiple cooling jackets 56a and 56b. The cooling jacket 56a is cooled by the cryogenic fluid with the lowest boiling temperature, and the cooling jacket 56b is cooled by the cryogenic fluid with the highest boiling temperature. The multiple cooling jackets 56 allow the heat load to be reduced in stages. The temperature of the inner surface of the middle shield 54 is thereby maintained at the boiling point of the lowest temperature cryogenic fluid.

An optional inner insulation layer 58 may be disposed inwardly from the middle shield 54. The inner insulation layer 58 is generally required in embodiments that utilize superconductive materials that are required to be maintained at a temperature lower than the boiling point of the cryogenic fluids. In these embodiments, the inner insulation layer 58 insulates the superconducting magnet system 12 from the temperature affects of the middle shield 54.

In a particular embodiment, liquid oxygen and liquid hydrogen are used as the cryogenic fluids. The liquid oxygen and liquid hydrogen are stored in the cryogenic tanks 30 and 32. The liquid oxygen is circulated through the cooling jacket 56b to reduce the temperature to approximately 90 K. The liquid hydrogen is circulated through the cooling jacket 56a to reduce the temperature to approximately 20 K.

It will be understood that the shielding system 50 may include other suitable devices and systems without departing from the scope of the present invention. For example, additional insulation and shield layers may be utilized to further insulate the superconducting magnet system 12 from the temperature affects of the downhole environment.

Figure 6:
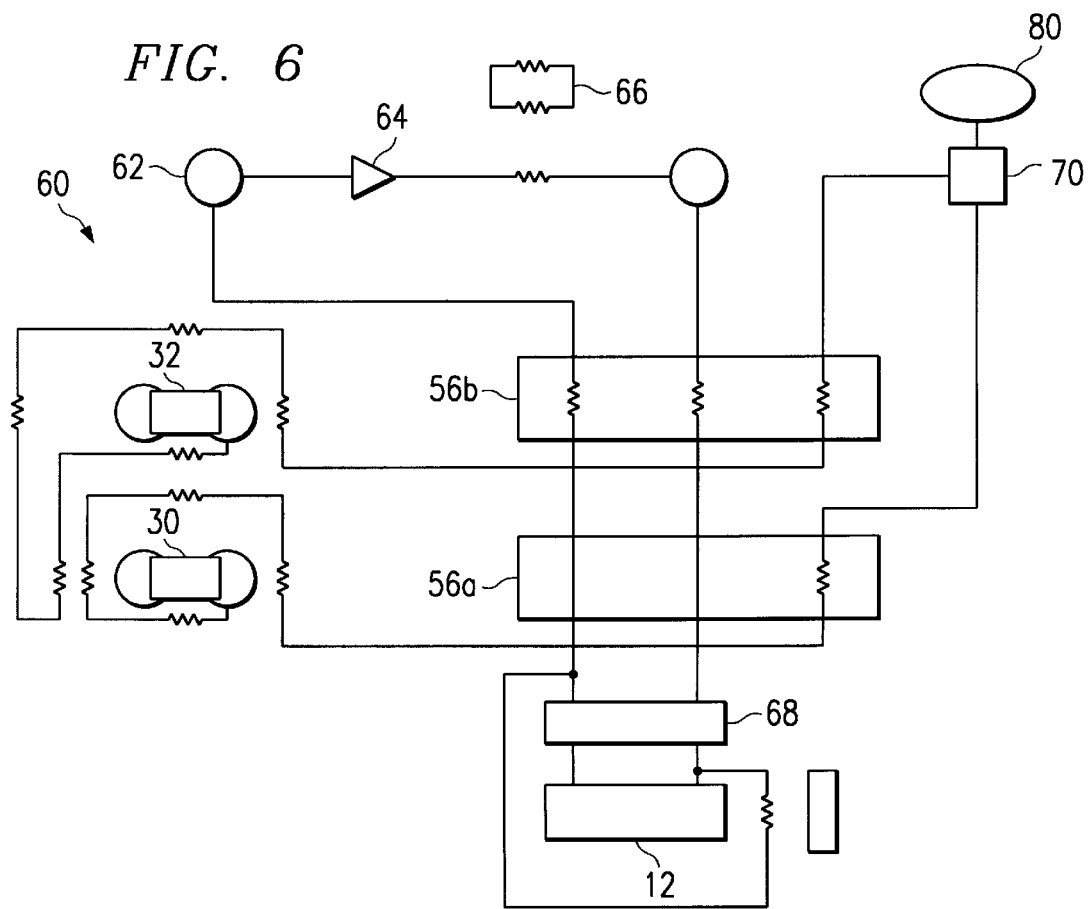
FIG. 6 is a heat circuit diagram illustrating the cryogenic cooling system in accordance with the present invention.

FIG. 6 is a heat circuit diagram illustrating the cryogenic cooling system 16 according to one embodiment of the present invention. In this embodiment, the cryogenic cooling system 16 comprises a refrigeration system 60 to reduce the temperature of the superconducting magnet system 12 to a temperature below the boiling temperature of the cryogenic fluids. The refrigeration system 60 circulates a cryogenic fluid, such as helium, through the superconducting magnet system 12 such that the cryogenic fluid is allowed to vaporize by boiling. In the case of helium, the boiling point is approximately 4 K. The cryogenic fluid must then be repressurized and cooled to allow the cryogenic fluid to be reused.

In the particular embodiment of the refrigeration system 60 illustrated in FIG. 6, helium is initially contained within a tank 62 that is maintained at ambient downhole temperatures. The helium flows through a compressor 64 and is compressed. The helium then flows through an ambient heat exchanger 66 to reduce the temperature of the helium to the ambient downhole temperature. The helium then flows through the cooling jacket 56b in which oxygen is used to reduce the temperature of the helium to approximately 90 K. The helium then flows through the cooling jacket 56a in which hydrogen is used to reduce the temperature of the helium to approximately 20 K. The helium then flows through a pulse tube cryopump 68 and circulated through the superconducting magnet system 12. The helium is then circulated back through the cooling jackets 56a and 56b of the middle shield 54 to the tank 62.

FIG. 6 also illustrates the heat load circuit of the cryogenic fluids and their removal by the power system 18. The cryogenic fluids cannot generally be discharged into the borehole because of the high pressures within the borehole. Without the removal of the gaseous cryogenic fluids, however, the pressures within the cryogenic cooling system 16 would equalize such that the cryogenic fluids would no longer vaporize. It is therefore necessary to remove the gaseous cryogenic fluids.

In an embodiment utilizing oxygen and hydrogen, the liquid oxygen is stored in the oxidizer cryogenic tank 32, and liquid hydrogen is stored in the fuel cryogenic tank 30. The liquid oxygen and liquid hydrogen flows through the cooling jackets 56a and 56b of the middle shield 54. In one embodiment, as discussed in greater detail below, the oxygen and hydrogen is then circulated to the power system 18. In this embodiment, the oxygen and hydrogen are used in a fuel cell 70 to produce electricity. The discharge from the fuel cell 70 is water. The water must be removed to prevent the vapor pressure of the water, approximately 9 atmospheres, from exceeding the inlet pressure of the oxygen and hydrogen entering the fuel cell 70. Other methods of removing the cryogenic fluids may be utilized. For example, the cryogenic fluids may be combusted and the combustion product stored.

It will be understood that the cryogenic cooling system 16 may comprise other suitable devices and systems without departing from the scope of the present invention. For example, the cryogenic cooling system 16 may include an electric cooling system to maintain the cryogenic tanks 30 and 32 at a cryogenic temperature.

Figure 7:
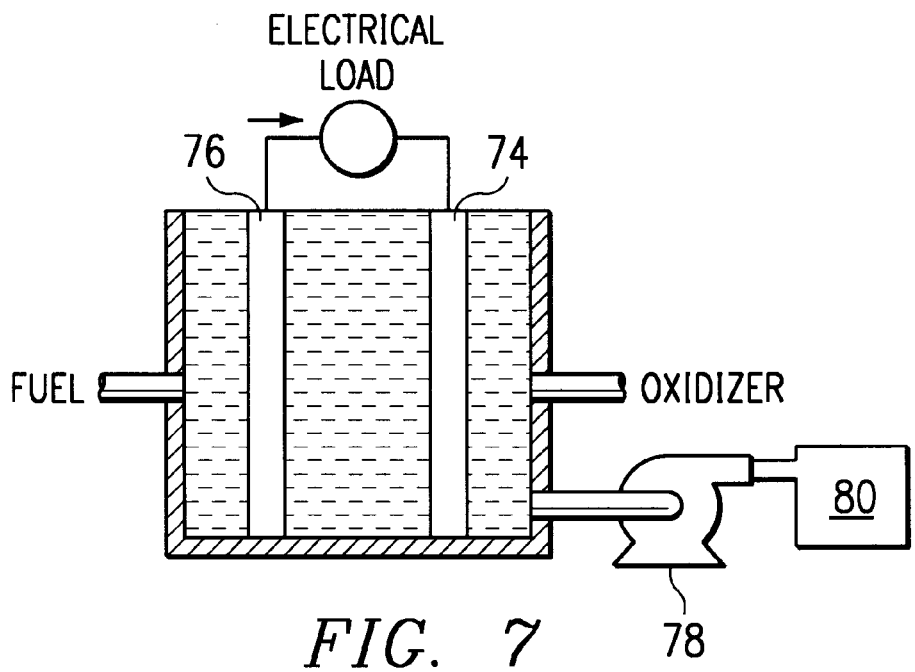
FIG. 7 is a schematic diagram of a power system, and illustrates an internal power supply comprising a fuel cell in accordance with the present invention.

FIG. 7 is a schematic diagram of the power system 18, and illustrates an internal power supply comprising a fuel cell 70. The fuel cell 70 generates electricity by reacting a fuel and an oxidizer. Electricity generated by the fuel cell 70 is directed to various components of the magnetic resonance logging instrument 10. In this embodiment, the electricity produced by the fuel cell 70 supplements the electricity supplied by the tether 34, thereby reducing the electrical load that is required to be conducted through the tether 34.

In one embodiment, the power system 18 comprises a hydrogen and oxygen fuel cell. In this embodiment, the hydrogen and oxygen from the cryogenic cooling system 16 are electrochemically combined within the fuel cell 70 to produce electricity.

The fuel cell 70 is comprised of an electrolyte material 72 between a cathode 74 and an anode 76. Hydrogen gas from the cryogenic cooling system 16 enters the fuel cell 70 and moves through the anode 76, where the hydrogen combines with the oxygen to produce water and an electron. An electric current is created as the electrons pass through an external circuit The power system 18 may also include a water pump 78 to pump the by-product water from the fuel cell 70 to a water storage tank 80.

Although the fuel cell 70 has been described in terms of a hydrogen and oxygen fuel cell 70, it will be understood that the fuel cell 70 may be of any type without departing from the scope of the present invention. For example, the fuel cell 70 may be an alkaline fuel cell, a polymer exchange membrane fuel cell, a phosphoric acid fuel cell, a molten carbonate fuel cell, or a solid oxide fuel cell.

It will be understood that the power system 18 may comprise other systems and devices without departing from the scope of the present invention. For example, the power system 18 may include a battery system, a generator system powered by hydrogen and oxygen, or any other suitable electricity generating device.

Figure 8:
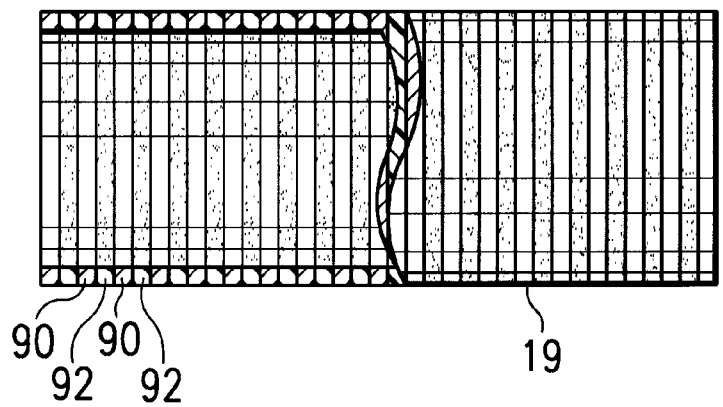
FIG. 8 is a cross-sectional diagram of a housing for the magnetic resonance logging instrument in accordance with the present invention.

FIG. 8 is a cross-sectional diagram of the housing 19. In one embodiment, the housing 19 is fabricated from a lamination of a number of high strength metal washers 90 separated from one another by a non-conducting layer 92. The high strength metal washers 90 provide the structural strength for the housing 19 to withstand the pressures and temperatures of the downhole environment. The non-conducting washers layer 92 prevents electrical current from being conducted along the longitudinal length of the housing 19. In a particular embodiment, the housing 19 is fabricated by a process in which the high strength metal washers 90 are stacked, prestressed, and bonded in a two-stage silicon process that forms the non-conducting layer 92 between the high strength metal washers 90. It will be understood that the housing 19 may be otherwise configured and fabricated without departing from the scope of the present invention.

The non-conducting housing 19 helps prevents attenuation of the RF field that is generated from the drive antenna 24. This is accomplished by increasing the radial gap between the drive antenna 24 and any longitudinal conductive surface that can produce image eddy-currents.

Although the present invention has been described with several embodiments, various changes and modifications may be suggested to one skilled in the art. It is intended that the present invention encompass such changes and modifications that follow within the scope of the appended claims.

What is claimed is:

1. A magnetic resonance logging instrument comprising:
   a housing;
   a superconducting magnet system disposed within the housing and operable to produce an external magnetic field;
   an antenna system disposed, in part, within the housing and coupled to the superconducting magnet system, the antenna system operable to produce and sense a radio frequency magnetic field;
   a cryogenic cooling system disposed within the housing and operable to cool the superconducting magnet system, wherein the cryogenic cooling system includes a shield system operable to insulate the superconducting magnet system; and a power system operable to supply power to the superconducting magnet system.

2. The magnetic resonance logging instrument of claim 1, wherein the superconducting magnet system comprises a main superconducting magnet and a pair of bump superconducting magnets.

3. The magnetic resonance logging instrument of claim 1, wherein the superconducting magnet system can produce a dipole and multipole magnetic field.

4. The magnetic resonance logging instrument of claim 1, wherein the antenna system comprises a separate drive antenna and sense antenna.

5. The magnetic resonance logging instrument of claim 4, wherein the sense antenna is a segmented sense antenna.

6. The magnetic resonance logging instrument of claim 1, further comprising a refrigeration system.

7. The magnetic resonance logging instrument of claim 1, wherein the power system comprises a combination of internal and external power systems.

8. The magnetic resonance logging instrument of claim 7, wherein the internal power is generated by a fuel cell.

9. A magnetic resonance logging instrument comprising:

a non-conducting housing;

a fuel cell disposed within the housing and operable to produce electricity;

a superconducting magnet system disposed within the housing and operable to produce a static magnetic field;

an oxygen and hydrogen cryogenic cooling system and operable to cool the superconducting magnet system;

a drive antenna coupled to the superconducting magnet system and operable to produce a radio frequency magnetic field orthogonal to the static magnetic field; and a sense antenna operable to receive a radio frequency magnetic field signal.

10. The magnetic resonance logging instrument of claim 9, wherein the superconducting magnet system comprises a main superconducting magnet and a pair of bump superconducting magnets.

11. The magnetic resonance logging instrument of claim 9, wherein the superconducting magnet system can be configured in a dipole and multipole configuration.

12. The magnetic resonance logging instrument of claim 9, wherein the sense antenna is a segmented sense antenna.

13. The magnetic resonance logging instrument of claim 9, wherein the cryogenic cooling system comprises a shield system.

14. The magnetic resonance logging instrument of claim 9, further comprising a refrigeration system.

* * * * *